(12) United States Patent
Park et al.

(10) Patent No.: US 11,969,213 B2
(45) Date of Patent: Apr. 30, 2024

(54) METHOD FOR SUPPORTING PREDICTION OF VASCULAR DISEASE USING FUNDUS IMAGE, APPARATUS THEREFOR AND SYSTEM INCLUDING THE SAME

(71) Applicant: XAIMED Co., Ltd., Seoul (KR)

(72) Inventors: Sang Min Park, Seoul (KR); Joo Young Chang, Seoul (KR); Choong Hee Lee, Seoul (KR); Il Hyung Shin, Jeju-si (KR)

(73) Assignee: XAIMED CO., LTD., Seoul (KR)

( * ) Notice: Subject to any disclaimer, the term of this patent is extended or adjusted under 35 U.S.C. 154(b) by 520 days.

(21) Appl. No.: 17/315,318

(22) Filed: May 9, 2021

(65) Prior Publication Data
US 2021/0378510 A1  Dec. 9, 2021

(30) Foreign Application Priority Data
Jun. 5, 2020  (KR) .................. 10-2020-0068154

(51) Int. Cl.
*A61B 3/12*  (2006.01)
*A61B 3/00*  (2006.01)
*G06N 20/00*  (2019.01)

(52) U.S. Cl.
CPC .......... *A61B 3/1241* (2013.01); *A61B 3/0025* (2013.01); *A61B 3/0041* (2013.01); *G06N 20/00* (2019.01)

(58) Field of Classification Search
CPC ... A61B 3/1241; A61B 3/0025; A61B 3/0041; A61B 3/14; A61B 5/004; A61B 5/02007; A61B 5/7275; G06N 20/00; G06N 3/044; G06N 3/045; G06N 3/08; G06T 2207/10024; G06T 2207/20081; G06T 2207/30041; G06T 2207/30101; G06T 7/0012; G06T 7/13; G06T 7/62; G06T 3/40; G16H 50/50; G16H 50/20; G16H 50/30; G16H 30/40
USPC ......................................... 351/206
See application file for complete search history.

(56) References Cited

U.S. PATENT DOCUMENTS

| | | | | |
|---|---|---|---|---|
| 11,200,665 B2* | 12/2021 | Jia | .................. | G06F 18/2163 |
| 2015/0110368 A1* | 4/2015 | Solanki | .................. | G16H 30/20 |
| | | | | 382/128 |
| 2019/0221313 A1* | 7/2019 | Rim | .................. | G06F 18/217 |
| 2020/0160999 A1* | 5/2020 | Rim | .................. | G06V 20/698 |
| 2020/0202527 A1* | 6/2020 | Choi | .................. | G06V 10/82 |

(Continued)

FOREIGN PATENT DOCUMENTS

KR   10-2013-0000576 A   1/2013
KR   10-1848321 B1   4/2018
(Continued)

*Primary Examiner* — William R Alexander
(74) *Attorney, Agent, or Firm* — Han's Law Office

(57) ABSTRACT

Provided are apparatuses, a non-transitory computer-readable medium or media, and methods for supporting predicting of vascular disease using a fundus image of a subject. In certain aspects, disclosed a method including the steps of: extracting a feature information from a first fundus image of the subject based on a machine learning model; generating a second fundus image having a feature which is corresponding to the feature information by mapping a saliency factor to the first fundus image; and displaying the first fundus image and the second fundus image on a display device.

14 Claims, 10 Drawing Sheets

(56) References Cited

U.S. PATENT DOCUMENTS

| | | | | |
|---|---|---|---|---|
| 2020/0288972 | A1* | 9/2020 | Park | A61B 3/14 |
| 2021/0327062 | A1* | 10/2021 | Choi | G06V 40/18 |
| 2022/0230750 | A1* | 7/2022 | Rim | G06T 7/0012 |
| 2022/0301153 | A1* | 9/2022 | Chen | A61B 5/0077 |
| 2022/0301709 | A1* | 9/2022 | Choi | A61B 5/021 |
| 2023/0162359 | A1* | 5/2023 | Choi | G16H 50/20 |
| | | | | 382/128 |

FOREIGN PATENT DOCUMENTS

| | | |
|---|---|---|
| KR | 10-2019-0074477 A | 6/2019 |
| KR | 10-2071774 B1 | 1/2020 |

* cited by examiner

METHOD FOR SUPPORTING PREDICTION OF VASCULAR DISEASE USING FUNDUS IMAGE, APPARATUS THEREFOR AND SYSTEM INCLUDING THE SAME

A. Technical Field

The present disclosure relates to diagnosing vascular disease of biometric images, more particularly, to an apparatus and method for supporting prediction of vascular disease using fundus images.

B. Description of the Related Art

Cardiovascular disease (CVD) is the most common cause of death worldwide and accounts for about 30% of all deaths, so evaluation and prevention of cardiovascular risk is of great clinical importance.

With development of artificial intelligence learning models, many machine learning models are being used to read medical images. In particular, in a fundus image of the medical images, the machine learning models are currently being used to support an image reading, an image finding, an image diagnosis in order to predict a disease of a patient. More specifically, a method of supporting the image reading, the image finding, the image diagnosis of the fundus image is to obtain the fundus image from the patient, extract feature from the fundus image based on the machined learning models, provide the feature to a practitioner, and predict the patient's disease based on it. In this case, the feature includes various information for the fundus image.

However, even if the feature of the fundus image is extracted based on the machine learning model, if the learning information input to the machine learning model is inadequate or insufficient for various factors, an entity such as a medical practitioner can receive incorrect information from the machined learning model.

Thus, even though the quality of the learning information is poor, there is a need for systems and methods that can do the more accurate prediction of the patient's disease using the learning information image and can explain why such the patient's disease was predicted. Also, when predicting a disease using the machine learning model, there is a need for a means to increase accuracy while reducing the amount of learning data for the machine learning model.

SUMMARY OF THE DISCLOSURE

In one aspect of the present disclosure, an apparatus for supporting predicting of vascular disease using a fundus image of a subject includes a processor and a memory including one or more sequences of instructions which, when executed by the processor, causes steps to be performed includes: extracting a feature information from a first fundus image of the subject based on a machine learning model, generating a second fundus image having a feature which is corresponding to the feature information by mapping a saliency factor to the first fundus image and displaying the first fundus image and the second fundus image on a display device.

Desirably, the steps further may include generating images in which a specific area of each of the first fundus image and the second fundus image is enlarged and displaying the images on the display device.

Desirably, the steps further may include generating a third fundus image which is visualized, by performing image processing so that the first fundus image and the second fundus image overlap and displaying the third fundus image on the display device.

Desirably, the steps further may include generating a pre-first fundus image by pre-processing on the first fundus image so that a specific area of the first fundus image is enlarged or partially partitioned.

In another aspect of the present disclosure, a non-transitory computer-readable medium or media include one or more sequences of instructions which, when executed by a processor, causes steps for supporting reading of a fundus image of a subject, includes extracting a feature information from a first fundus image of the subject based on a machine learning model, generating a second fundus image having a feature which is corresponding to the feature information by mapping a saliency factor to the first fundus image and displaying the first fundus image and the second fundus image on a display device.

BRIEF DESCRIPTION OF THE DRAWINGS

References will be made to embodiments of the disclosure, examples of which may be illustrated in the accompanying figures. These figures are intended to be illustrative, not limiting. Although the disclosure is generally described in the context of these embodiments, it should be understood that it is not intended to limit the scope of the disclosure to these particular embodiments.

DETAILED DESCRIPTION OF PREFERRED EMBODIMENTS

Figure 1:
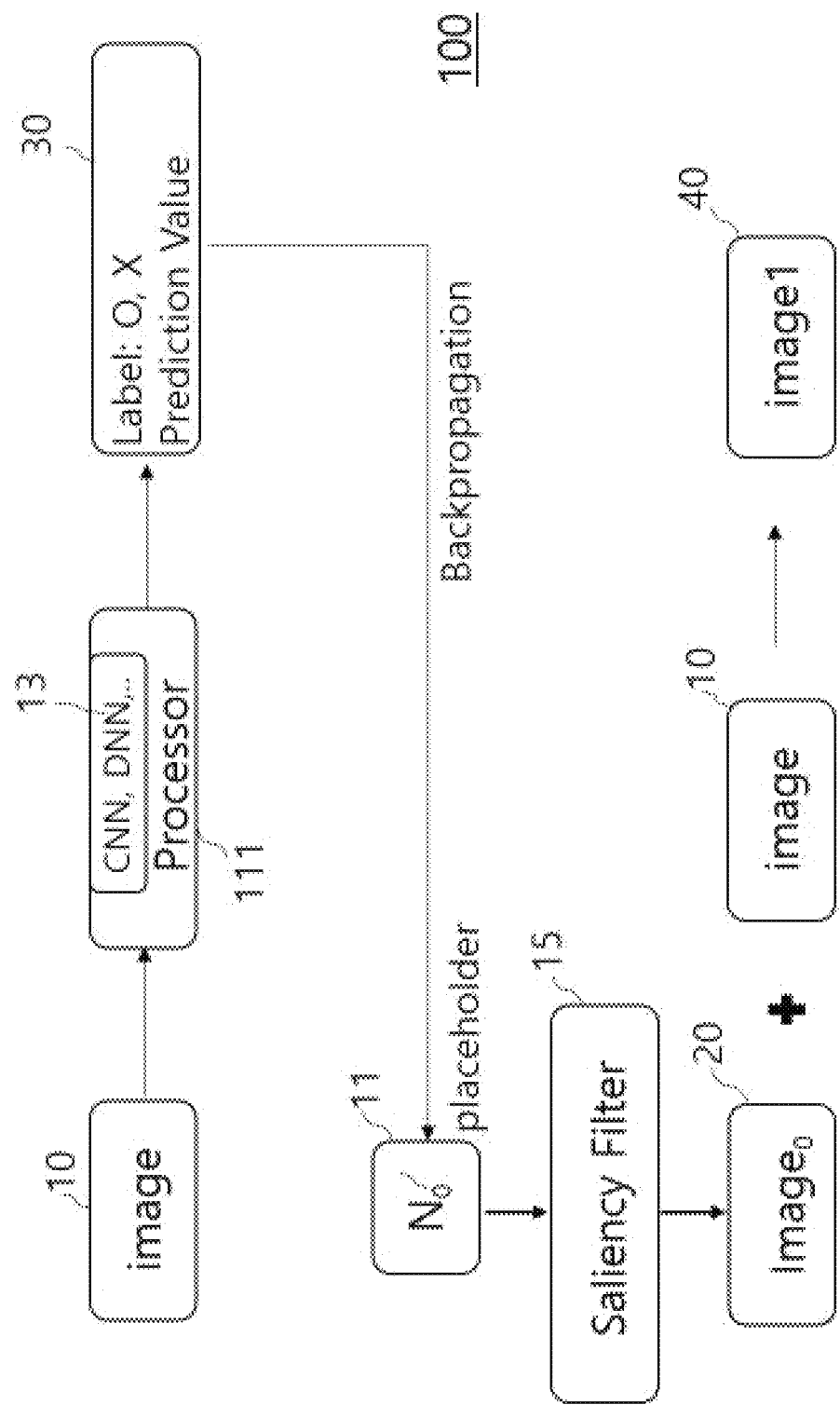
FIG. 1 shows a flowchart of an illustrative process for generating a feature information of a fundus image according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof.

It shall also be noted that the terms "coupled," "connected," "linked," or "communicatively coupled" shall be understood to include direct connections, indirect connections through one or more intermediary devices, and wireless connections.

Furthermore, one skilled in the art shall recognize: (1) that certain steps may optionally be performed; (2) that steps may not be limited to the specific order set forth herein; and (3) that certain steps may be performed in different orders, including being done contemporaneously.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments.

In the following description, it shall also be noted that the terms "learning" shall be understood not to intend mental action such as human educational activity because of referring to performing machine learning by a processing module such as a processor, a CPU, an application processor, micro-controller, so on.

An "image" is defined as a reproduction or imitation of the form of a person or thing, or specific characteristics thereof, in digital form. An image can be, but is not limited to, a JPEG image, a PNG image, a GIF image, a TIFF image, or any other digital image format known in the art. "Image" is used interchangeably with "photograph".

A "feature(s)" is defined as a group of one or more descriptive characteristics of subjects that can discriminate for disease. A feature can be a numeric attribute.

The terms "comprise/include" used throughout the description and the claims and modifications thereof are not intended to exclude other technical features, additions, components, or operations.

Unless the context clearly indicates otherwise, the singular forms "a," "an," and "the" are intended to include the plural forms as well. Also, when description related to a known configuration or function is deemed to render the present disclosure ambiguous, the corresponding description is omitted.

FIG. 1 shows a flowchart of an illustrative process for generating a fundus image including feature information by an apparatus 100 according to embodiments of the present disclosure. As depicted, in embodiments, a processor 111 may extract a feature information 30 from a first fundus image 10 that is photographed by imaging means such as a camera, using a machine learning model 13 (e.g., CNN, DNN, etc.). The extracted feature information 30 may be stored in a memory unit 113 or a storage device 115 described below. In embodiments, the machine learning model 13 may be installed into a processor 111 and executed by the processor 111. The machine learning model 13 may be installed into a computer-readable medium or media (not shown in FIG. 1) and executed by the computer-readable medium or media. In alternative embodiments, the machine learning model 13 may be installed into the memory unit 113 or the storage device 115 and executed by the processor 111.

In addition, the processor 111 may store clinical information of a subject (e.g., a patient) in the memory unit 113 or the storage device 115 in advance. In embodiments, the processor 111 may extract the feature information of the first fundus image 10 based on the machine learning model 13 by using the clinical information of the subject stored in the memory unit 113 or the storage device 115. In embodiments, the clinical information may be, but is not limited to, the age, sex, medical history, questionnaire information, test measurement values, exercise habits, eating habits, family history related to the medical history, alcohol consumption, smoking status. In embodiments, the questionnaire information may include neuromedical questionnaire that a practitioner (e.g., a medical doctor) can perform on the subject or may mean ideal findings currently observed to the subject, unlike medical history thereof. In embodiments, the test measurement values may include an intraocular pressure, a blood pressure, a blood sugar level, and the like.

In embodiments, the feature information 30 may be various information that it can support an entity (e.g., a practitioner or a computing device) reading an fundus image such as predicting or diagnosing disease. For instance, when predicting or diagnosing cardiovascular disease (CVD) like atherosclerosis in the fundus image of the subject, the feature information may include at least one of various information such as a retinal vessel information, a macula information including a fovea, a cotton wool spot information and an optic nerve change information included in the fundus image. In embodiments, the retinal vessel information may include at least one of a thickness of the retinal vessel, an expansion rate of the retinal vessel, a propagation speed of the retinal vessel expansion and a degree of elasticity of the retinal vessel according to the propagation speed of the retinal vessel expansion. In embodiments, the optic nerve change information may include at least one of the increased C/D ratio (Cup-to-Disk ratio) information, thickness change information for disc rim thinning and contrast information for retinal nerve fiber layer defect.

In this case, in embodiments, on the results performed by the processor 111, the apparatus 100 may appear the finding (Label: O, X) indicating the presence or absence of a vascular disease in the fundus image on the basis of the feature information, or a prediction value indicating the presence or absence of the finding on a display device 130, 330 describe below. In embodiments, the prediction value may be expressed as a percentage or a number between 0 and 1, an explanation of presence or absence of the finding and the prediction value will be described in more detail below.

In embodiments, the processor 111 may map an saliency factor 11 into the first fundus image 10. By doing so, a second fundus image 20 including a feature corresponding to the feature information 30 of the first fundus image 10 may be generated. In embodiments, mapping the saliency factor 11 may be performed by the processor 111 using a saliency filter 15. In embodiments, the generated second fundus image 20 may be stored in the memory unit 113 or the storage device 115 described below.

In embodiments, the saliency factor 11 may include at least one of a value that adjusts the gradation level of the R, G, and B pixels representing the first fundus image 10, a value that adjusts the color of the R, G, and B pixels of the first fundus image 10, a value that locally adjusts the contrast ratio in the first fundus image 10 and a value that adjusts an orientation feature of the first fundus image 10. It should be noted that the saliency factor 11 may include any factor that can change the feature information of the first fundus image 10.

In embodiments, the second fundus image 20 may be generated by mapping the saliency factor 11 to the first fundus image 10 once. In alternative embodiments, the second fundus image 20 may be generated by repeatedly mapping the saliency factor 11 to the first fundus image 10 according to the prediction value obtained based on the machine learning model 13.

In embodiments, the first fundus image 10 having the feature information 30 obtained based on the machine learning model 13 and the second fundus image 20 having the feature corresponding to the feature information of the first fundus image 10 obtained by mapping the saliency factor 11 may be provided to at least one of a practitioner (e.g., a medical doctor) through a transmission module such as a display adapter 118 or a network adapter 119, one and more remote computing devices 200, 300, 400 that is linked to the computing device 110 through an Internet network, and the other device that can use the fundus image 10 and the second fundus image 20, described below.

In embodiments, since the second fundus image 20 has the feature corresponding to the feature information of the first fundus image 10, when the entity (e.g., the practitioner, the remote computing device) reads the first fundus image 10, the apparatus 100 may allow the entity to read the first fundus image 10 by comparing it with the second fundus image 20, so that the entity can easily and accurately read the first fundus image 10. In addition, since the processor 111 may generate a comparison image (i.e., the second fundus image 20) for the first fundus image 10, and compare the comparison image with the first fundus image 10, it is possible to convincingly explain the reason why such a reading result is obtained for the first fundus image 10. Accordingly, the reliability of the reading of the first fundus image 10 having the feature information 30 can be improved.

In addition, in embodiments, the apparatus 100 may generate the third fundus image 40 by performing an image processing so that the first fundus image 10 and the second fundus image 20 overlap each other. The third fundus image 40 may be displayed on the display device 130 for the entity. The third fundus image 40 may visually express a region in which features corresponding to the feature information of the first fundus image 10 are located in the fundus image. Thus, it is possible to accurately read the fundus image.

Figure 2:
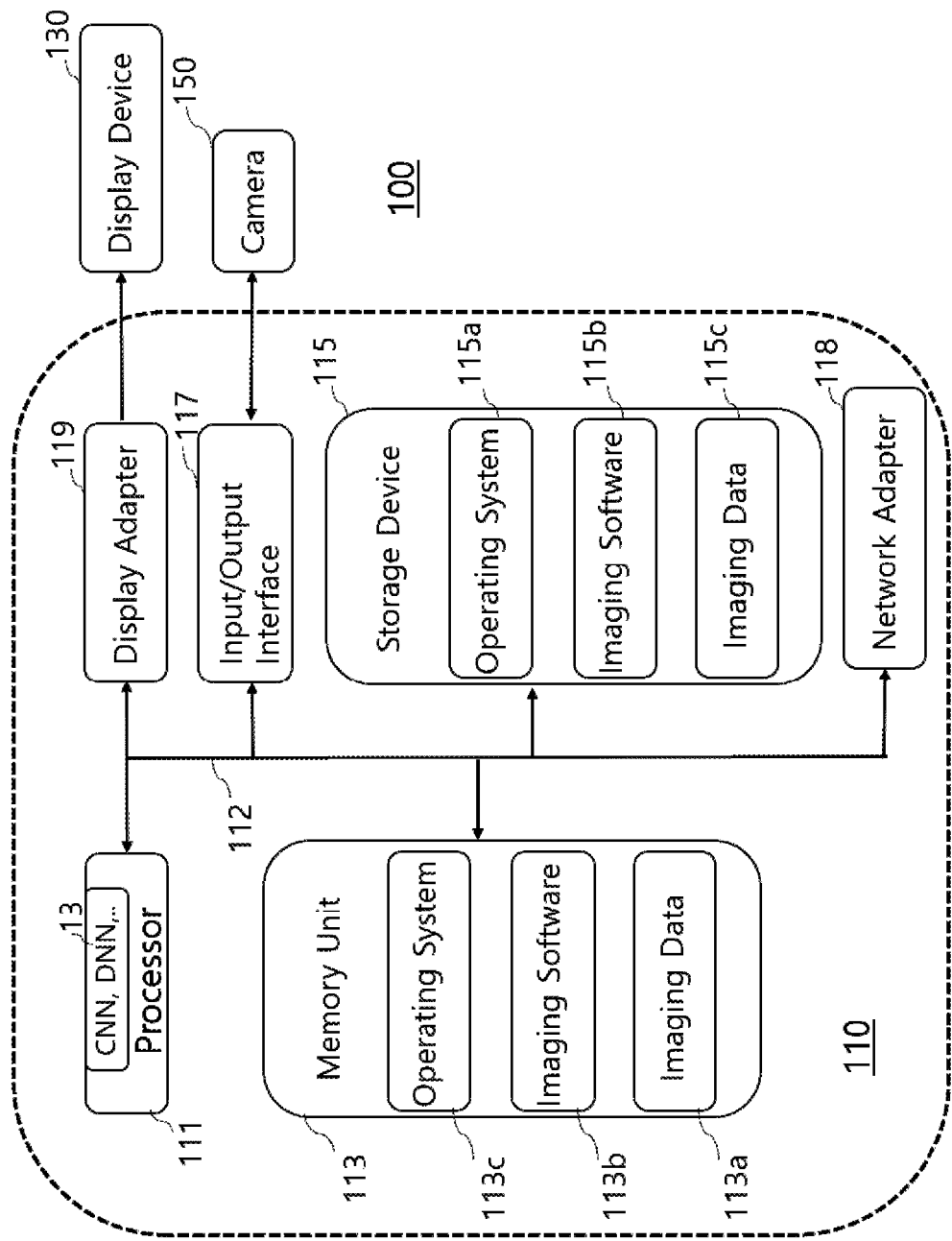
FIG. 2 shows a schematic diagram of an illustrative apparatus for supporting predicting of vascular disease using a fundus image according to embodiments of the present disclosure.

FIG. 2 is a schematic diagram of an illustrative apparatus 100 for supporting predicting of vascular disease using a fundus image according to embodiments of the present disclosure.

As depicted, the apparatus 100 may include a computing device 110, a display device 130 and a camera 150. In embodiments, the computing device 110 may include, but is not limited thereto, one or more processor 111, a memory unit 113, a storage device 115, an input/output interface 117, a network adapter 118, a display adapter 119, and a system bus 112 connecting various system components to the memory unit 113. In embodiments, the apparatus 100 may further include communication mechanisms as well as the system bus 112 for transferring information. In embodiments, the communication mechanisms or the system bus 112 may interconnect the processor 111, a computer-readable medium, a short range communication module (e.g., a Bluetooth, a NFC), the network adapter 118 including a network interface or mobile communication module, the display device 130 (e.g., a CRT, a LCD, etc.), an input device (e.g., a keyboard, a keypad, a virtual keyboard, a mouse, a trackball, a stylus, a touch sensing means, etc.) and/or subsystems. In embodiments, the camera 150 may include an image sensor (not shown) that captures an image of an subject and photoelectrically converts the image into an image signal, and may photograph a fundus image of the subject using the image sensor. The photographed fundus image may be stored in the memory unit 113 or the storage device 115, or may be provided to the processor 111 through the input/output interface 117 and processed based on the machine learning model 13.

In embodiments, the processor 111 is, but is not limited to, a processing module, a Computer Processing Unit (CPU), an Application Processor (AP), a microcontroller, a digital signal processor. In embodiments, the processor 111 may include an image filter such as a high pass filter or a low pass filter to filter a specific factor in a fundus image. In addition, in embodiments, the processor 111 may communicate with a hardware controller such as the display adapter 119 to display a user interface on the display device 130. In embodiments, the processor 111 may access the memory unit 113 and execute commands stored in the memory unit 113 or one or more sequences of instructions to control the operation of the apparatus 100. The commands or sequences of instructions may be read in the memory unit 113 from computer-readable medium or media such as a static storage or a disk drive, but is not limited thereto. In alternative embodiments, a hard-wired circuitry which is equipped with a hardware in combination with software commands may be used. The hard-wired circuitry can replace the soft commands. The instructions may be an arbitrary medium for providing the commands to the processor 111 and may be loaded into the memory unit 113.

In embodiments, the system bus 112 may represent one or more of several possible types of bus structures, including a memory bus or memory controller, a peripheral bus, an accelerated graphics port, and a processor or local bus using any of a variety of bus architectures. For instance, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. In embodiments, the system bus 112, and all buses specified in this description can also be implemented over a wired or wireless network connection.

A transmission media including wires of the system bus 112 may include at least one of coaxial cables, copper wires, and optical fibers. For instance, the transmission media may take a form of sound waves or light waves generated during radio wave communication or infrared data communication.

In embodiments, the apparatus 100 may transmit or receive the commands including messages, data, and one or more programs, i.e., a program code, through a network link or the network adapter 118. In embodiments, the network adapter 118 may include a separate or integrated antenna for enabling transmission and reception through the network link. The network adapter 118 may access a network and communicate with a remote computing devices 200, 300, 400 in FIG. 3.

In embodiments, the network may be, but is not limited to, at least one of LAN, WLAN, PSTN, and cellular phone networks. The network adapter 118 may include at least one of a network interface and a mobile communication module for accessing the network. In embodiments, the mobile communication module may be accessed to a mobile communication network for each generation such as 2G to 5G mobile communication network.

In embodiments, on receiving a program code, the program code may be executed by the processor 111 and may be stored in a disk drive of the memory unit 113 or in a non-volatile memory of a different type from the disk drive for executing the program code.

In embodiments, the computing device 110 may include a variety of computer-readable medium or media. The computer-readable medium or media may be any available medium or media that are accessible by the computing device 100. For example, the computer-readable medium or media may include, but is not limited to, both volatile and non-volatile media, removable or non-removable media.

In embodiments, the memory unit 113 may store a driver, an application program, data, and a database for operating the apparatus 100 therein. In addition, the memory unit 113 may include a computer-readable medium in a form of a volatile memory such as a random access memory (RAM), a non-volatile memory such as a read only memory (ROM), and a flash memory. For instance, it may be, but is not limited to, a hard disk drive, a solid state drive, an optical disk drive.

In embodiments, each of the memory unit 113 and the storage device 115 may be program modules such as the imaging software 113b, 115b and the operating systems 113c, 115c that can be immediately accessed so that a data such as the imaging data 113a, 115a is operated by the processor 111.

In embodiments, the machine learning model 13 may be installed into at least one of the processor 111, the memory unit 113 and the storage device 115. The machine learning model 13 may be, but is not limited to, at least one of a deep neural network (DNN), a convolutional neural network (CNN) and a recurrent neural network (RNN), which are one of the machine learning algorithms.

Figure 3:
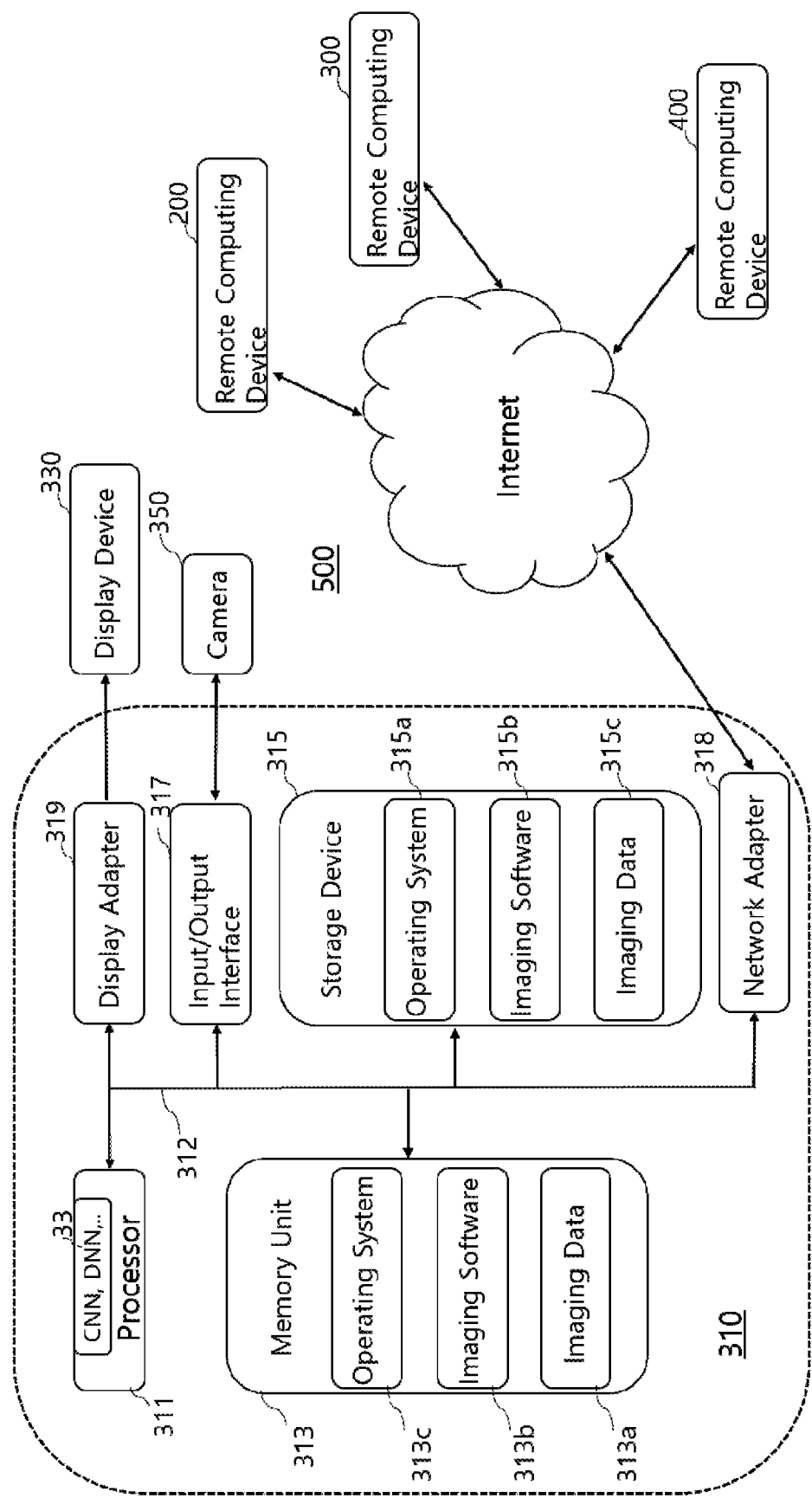
FIG. 3 shows a schematic diagram of an illustrative system for supporting predicting of vascular disease using a fundus image according to embodiments of the present disclosure.

FIG. 3 is a schematic diagram of an illustrative system 500 for supporting predicting of vascular disease using a fundus image according to embodiments of the present disclosure.

As depicted, the system 500 may include a computing device 310 and one and more remote computing devices 200, 300, 400. In embodiments, the computing device 310 and the remote computing devices 200, 300, 400 may be connected to each other through a network. The components 310, 311, 312, 313, 315, 317, 318, 319, 330 of the system 500 are similar to their counterparts in FIG. 2. In embodiments, each of remote computing devices 200, 300, 400 may be similar to the apparatus 100 in FIG. 2. For instance, each of remote computing devices 200, 300, 400 may include each of the subsystems, including the processor 311, the memory unit 313, an operating system 313c, 315a, an imaging software 313b, 315b, an imaging data 313a, 315c, a network adapter 318, a storage device 315, an input/output interface 317 and a display adapter 319. Each of remote computing devices 200, 300, 400 may further include a display device 330 and a camera 350. In embodiments, the system bus 312 may connect the subsystems to each other.

In embodiments, the computing device 310 and the remote computing devices 200, 300, 400 may be configured to perform one or more of the methods, functions, and/or operations presented herein. Computing devices that implement at least one or more of the methods, functions, and/or operations described herein may comprise an application or applications operating on at least one computing device. The computing device may comprise one or more computers and one or more databases. The computing device may be a single device, a distributed device, a cloud-based computer, or a combination thereof.

It shall be noted that the present disclosure may be implemented in any instruction-execution/computing device or system capable of processing data, including, without limitation laptop computers, desktop computers, and servers. The present invention may also be implemented into other computing devices and systems. Furthermore, aspects of the present invention may be implemented in a wide variety of ways including software (including firmware), hardware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 4:
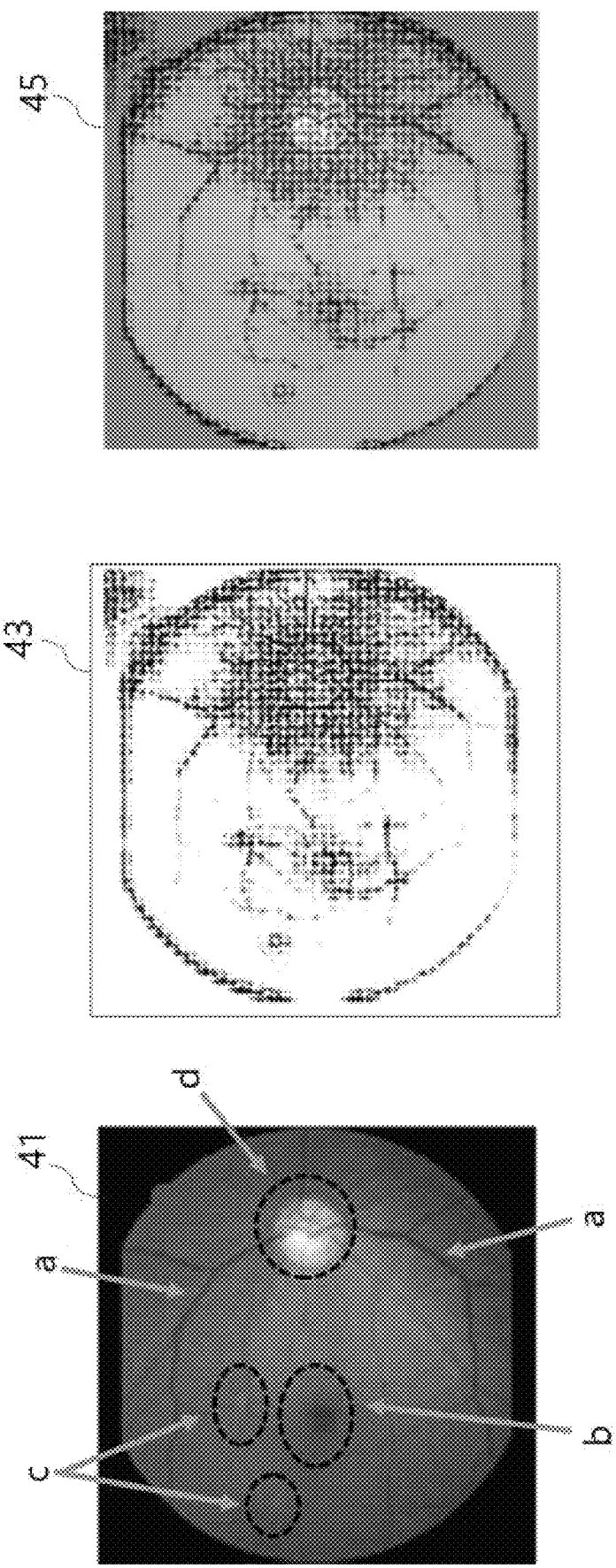
FIG. 4 is a view showing fundus images acquired by an apparatus according to embodiments of the present disclosure.

FIG. 4 is a view showing fundus images acquired by an apparatus 100 according to embodiments of the present disclosure.

As depicted, a first fundus image 41 is obtained from a subject (e.g., patient) based on the machine learning model 13 of the apparatus 100 in FIG. 1, a second fundus image 43 is obtained by mapping a saliency factor 11 to the first fundus image 41 and a third fundus image 45 is obtained by performing an image processing so that the first fundus image 41 and the second fundus image 43 overlap each other and are visualized.

The feature information of the first fundus image 41 is at least one of various information such as information of retinal vessel change (a), information of macular change including a fovea (b), information of cotton-wool spot (c) and information of optic nerve change (d). In the second fundus image 43, a region corresponding to a region where the feature information of the first fundus image 41 is located may be visualized. The method of mapping the saliency factor may be similar to mapping described in FIG. 1.

More specifically, the first fundus image 41 obtained based on the machine learning model 13 is a fundus image that can show the findings (a practitioner's opinion) in which it appears any vascular disease. However, on reading the first fundus image 41, the accuracy or reliability of such findings on the first fundus image 41 may be poor. In embodiments, the processor 111 may generate the second fundus image 43 and the third fundus image 45 so that a region that can support the prediction of vascular disease appears in the fundus image based on the feature information of the first fundus image 41. The second and third fundus images 43, 45 may be displayed on the display device 130 so that the entity can compare the first fundus image 41 with the second and third fundus images 43, 45. Since the apparatus 100 can allow the entity to compare the first fundus image with the second fundus image when reading the fundus image, the reliability and accuracy of a reading (e.g., a finding, a prediction, a diagnosis) on the first fundus image by the apparatus 100 can be improved. Thus, the apparatus 100 can allow the entity to explain the reason why such the reading was obtained.

Figure 5:
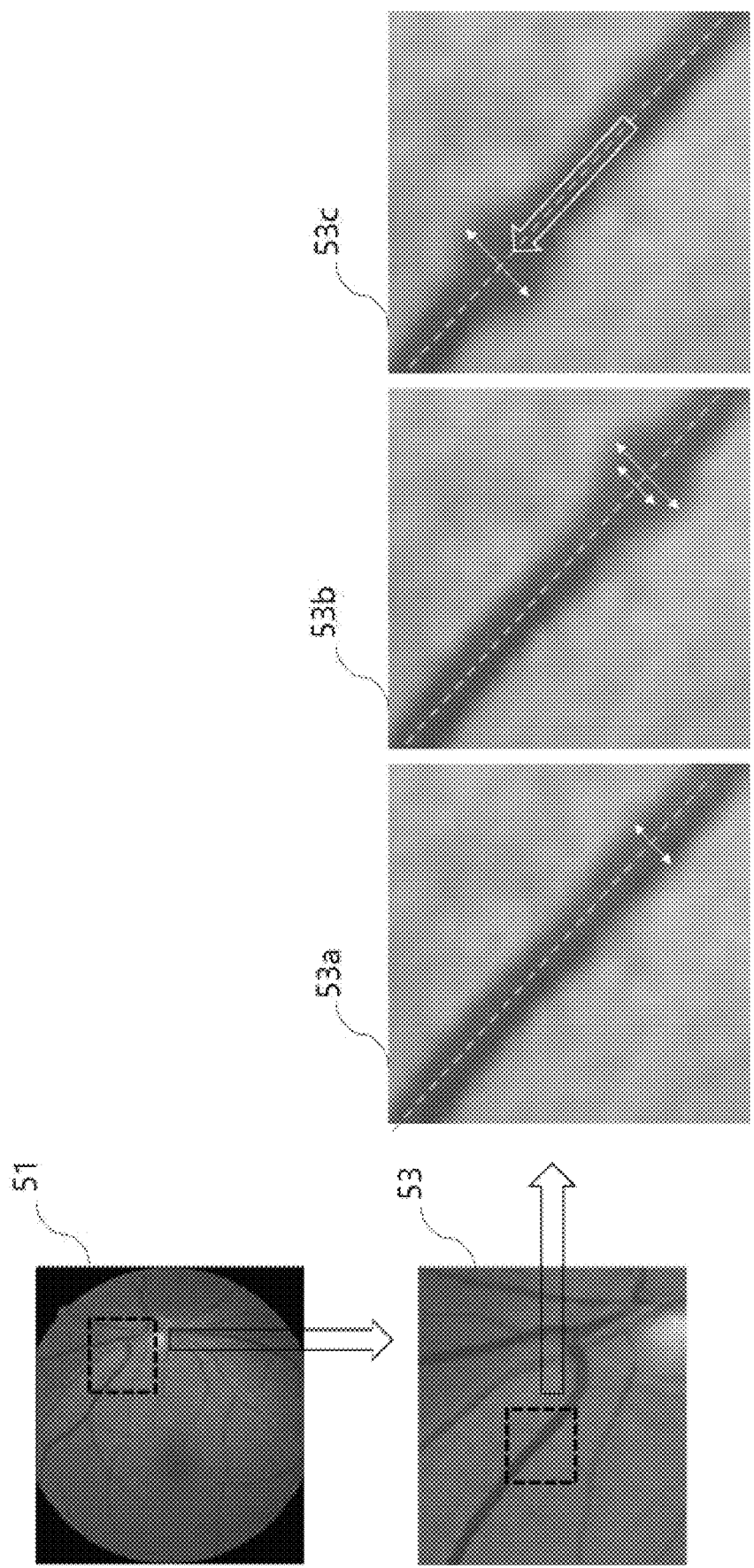
FIG. 5 is a view showing images including a retinal vessel acquired by an apparatus according to embodiments of the present disclosure.

FIG. 5 is a view showing fundus images including a retinal vessel acquired by an apparatus 100 according to embodiments of the present disclosure.

Referring to FIG. 5, a first fundus image 51 is obtained from the subject based on the machine learning model 13 of the apparatus 100 in FIG. 1, and an enlarged first image 53 is obtained by enlarging a retinal vessel area in the first fundus image 51. A further enlarged images 53a, 53b, 53c are images showing any changes in retinal vessels. The first vessel image 53a represents the retinal vessel thickness in the enlarged first image 53, the second vessel image 53b represents an expansion rate of the retinal vessel in the enlarged first image 53, and the third vessel image 53c represents a propagation speed of the retinal vessel expansion and a degree of elasticity of the retinal vessel based on the propagation speed of the retinal vessel expansion in the enlarged first image 53.

The thickness of the retinal vessel may represent a distance measured at the intersection of the outer wall of the retinal vessel and the line perpendicular to the center line of the retinal vessel. The expansion rate of the retinal vessel may represent a thickness change of the retinal vessel according to the temporal difference occurring at the same point of the retinal vessel. The propagation speed of the retinal vessel may represent a value obtained by dividing a distance at which the vascular expansion moves from one point to another point by the movement time, or a corresponding velocity value calculated using Fourier Transform equations.

Figure 6:
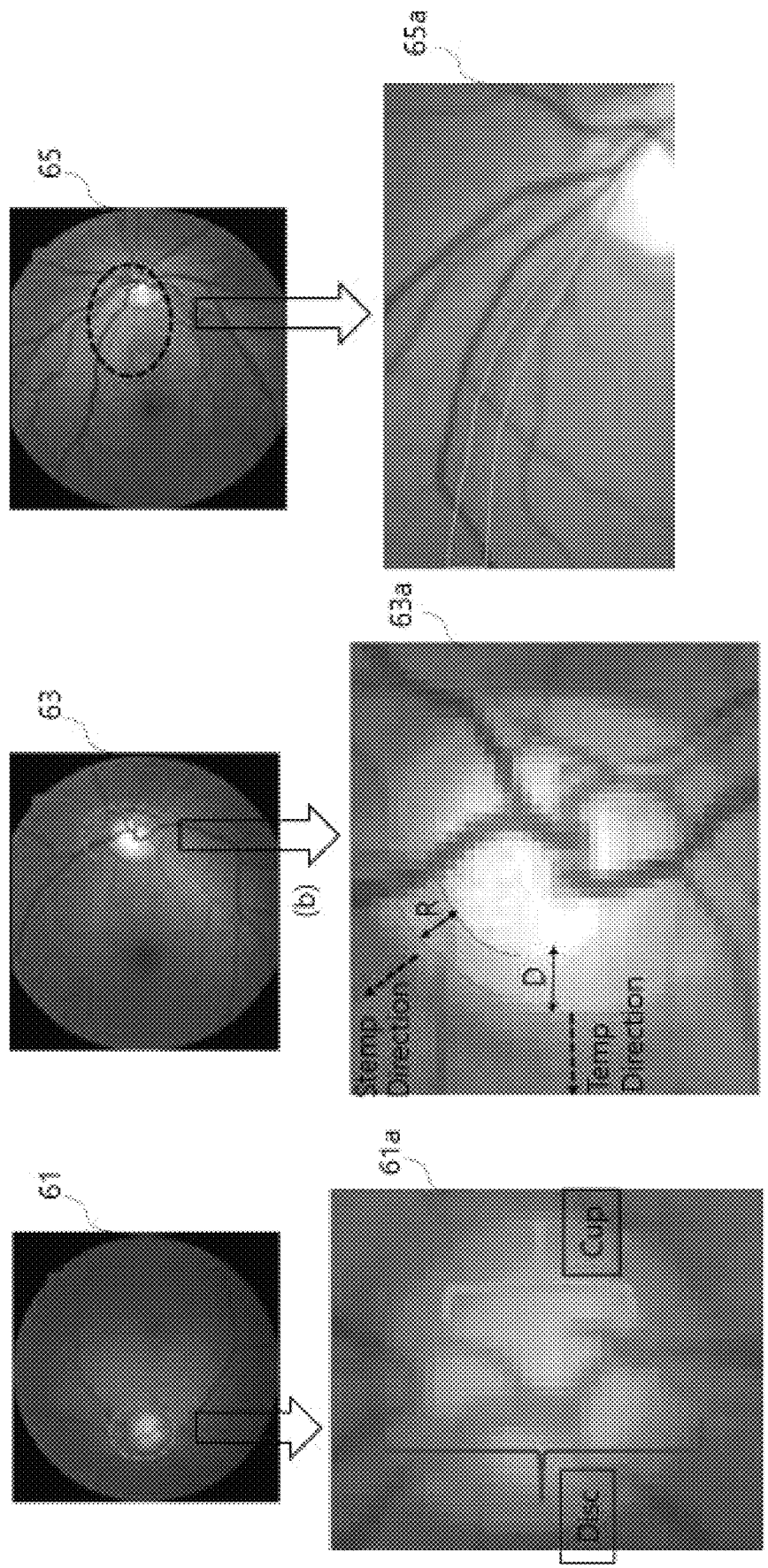
FIG. 6 is a view showing fundus images including information of an optic nerve change acquired by an apparatus according to embodiments of the present disclosure.

FIG. 6 is a view showing fundus images including information of an optic nerve change acquired by an apparatus 100 according to embodiments of the present disclosure.

As depicted, a first fundus image 61 including a C/D ratio information is obtained from the subject based on the machine learning model 13 of the apparatus 100, and an enlarged first image 61a is obtained by enlarging a cup and disc area in the first fundus image 61 in order to seek a value of the C/D ratio. The first fundus image 63 including a Disc Rim Thinning information is acquired by an apparatus 100, and an enlarged first image 63a is obtained by enlarging a cup and disc area in the first fundus image 63 in order to seek a value of the Disc Rim Thinning. The first fundus image 65 including a contrast information of a Retinal Nerve Fiber Layer Defect acquired by an apparatus 100, and an enlarged first image 65a is obtained by enlarging an area where the Retinal Nerve Fiber Layer Defect appears in the first fundus image 65 in order to seek a contrast ration of the value of the Retinal Nerve Fiber Layer.

A value of the C/D ratio is defined as the value of the maximum distance of an area corresponding to a cup in the fundus image divided by the maximum distance of an area corresponding to a disc in a fundus image. Typically, the value of the C/D ratio may be a measure of predicting a vascular disease in the fundus image.

The Rim is defined as an area excluding the area corresponding to the Cup in the Disc area of the fundus image and the Disc Rim Thinning is defined as the degree to which the thickness of the Rim changes in at least one of the Superiotemporal (or Stemp), Superior, Inferiotempal, and Inferior directions defined in the fundus image. Typically, when reading the fundus image, if at least one of the values of the thickness of the Rim in the Superiotemporal, Stemp, Superior, Inferiotempal, and Inferior directions divided by the thickness of the Rim in a Temporal (or Temp) direction is approximately 1.6 or less, or is less than 0.1 times the maximum length of the Disc, the entity has the finding in which there is a vascular disease in the fundus image.

The Retinal Nerve Fiber Layer (hereinafter, RNFL) appears in a fan shape from the disc along a blood vessel in the fundus image, the RNFL Defect means that the RNFL become defective or disappeared in the fundus image. When reading the fundus image, if an area of the RNFL appears dark on the fundus image and a bright pattern of the RNFL is lost, the entity has the finding in which there is a vascular disease in the fundus image.

Thus, the apparatus can directly predict a vascular disease of a subject through various change information of retinal vessels and also indirectly predict the vascular disease of the subject through change information of the optic nerve.

Figure 7A:
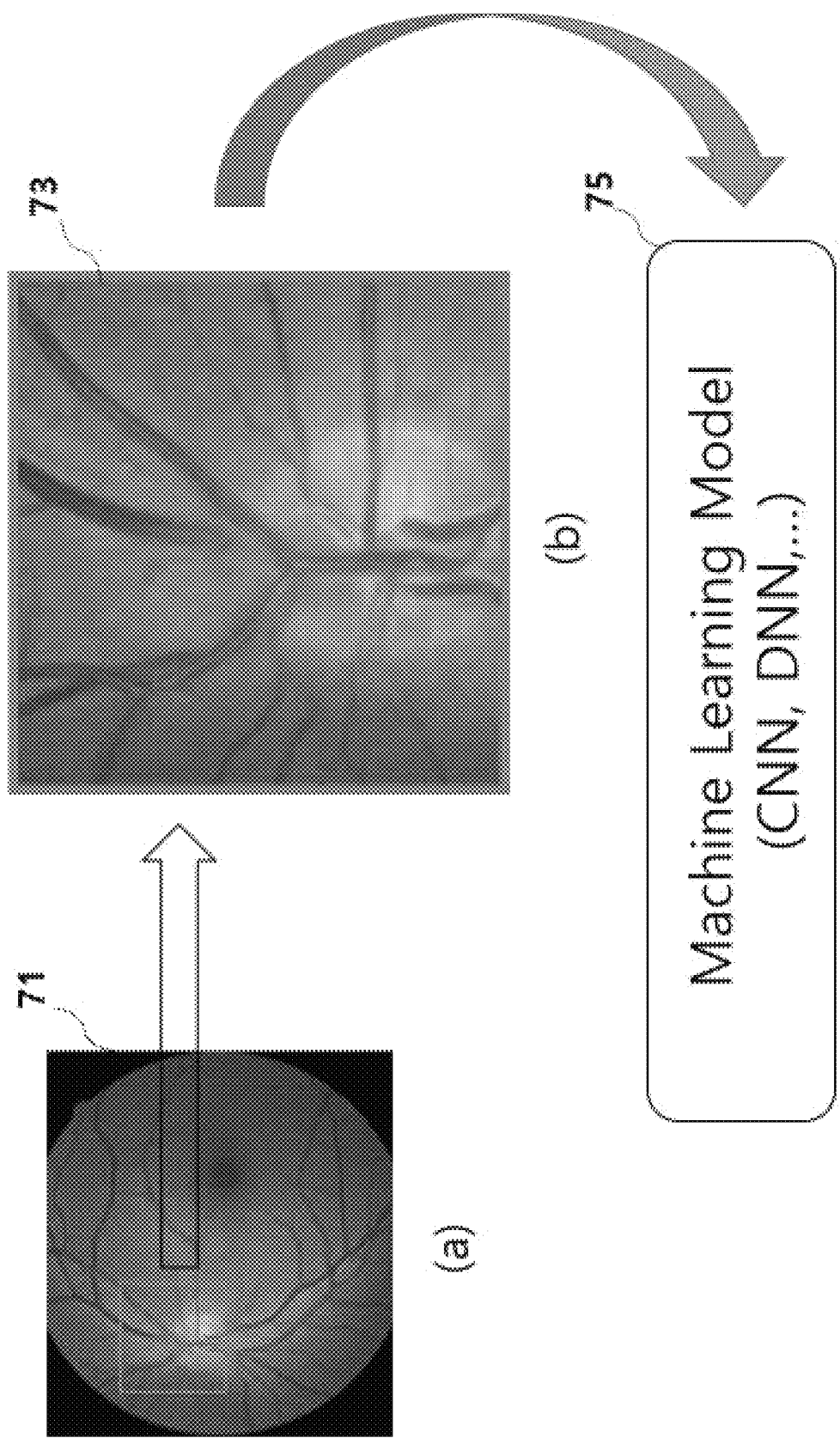
FIGS. 7A and 7B are a view showing an illustrative process for generating a pre-fundus image by apparatus according to embodiments of the present disclosure.
Figure 7B:
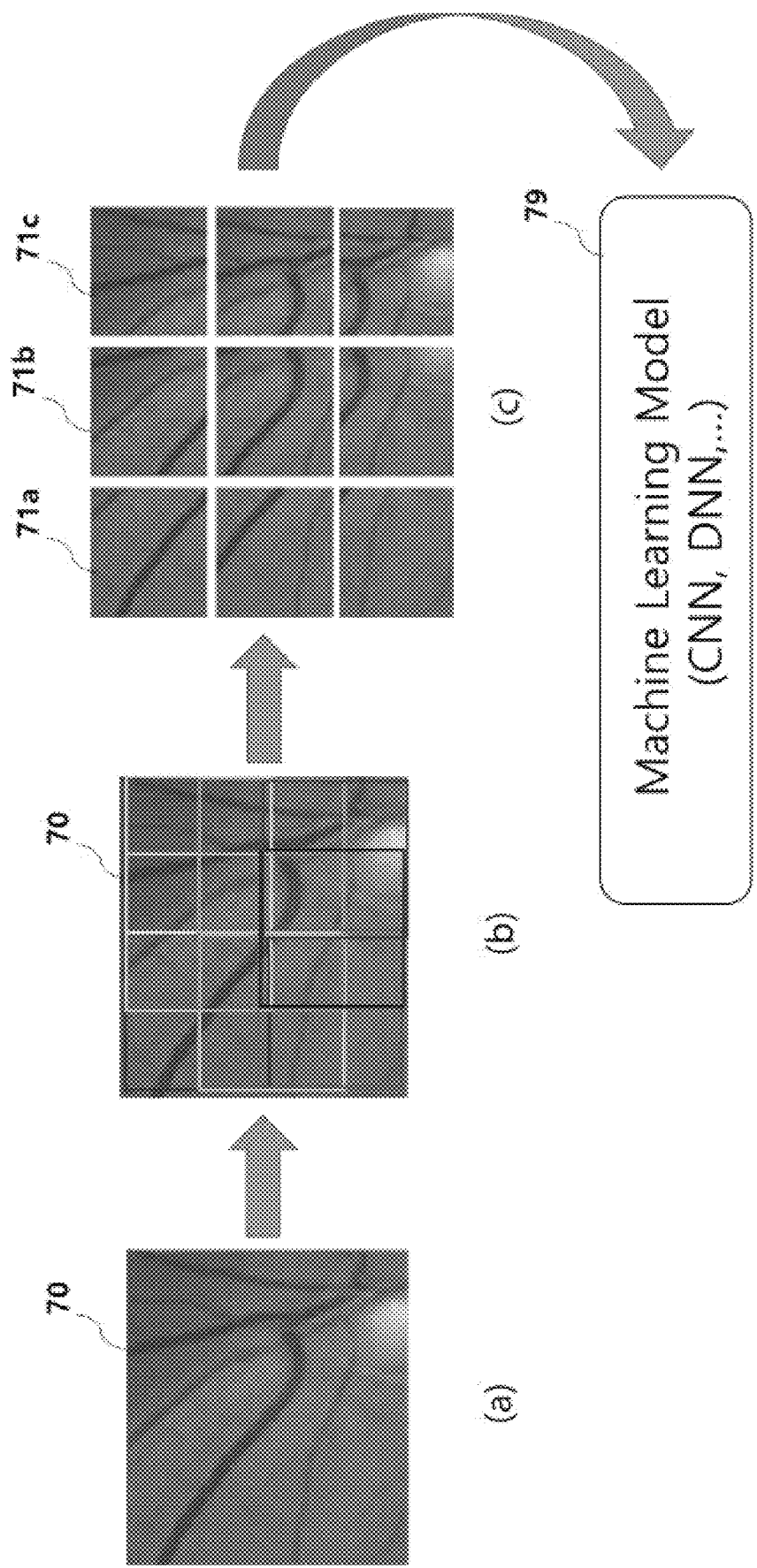

FIGS. 7A and 7B are a view showing an illustrative process for generating a pre-fundus image by apparatus 100 according to embodiments of the present disclosure.

As depicted in FIG. 7A, in embodiments, initially an original fundus image 71 of the subject may be obtained by taking an image by a camera (not shown). After that, pre-fundus image 73 may be generated by pre-processing on the original fundus image 71 by the processor 111 in FIG. 1 so that a specific region of the original fundus image is enlarged in order to more intensively check a feature information on the original fundus image 71. In this case, the specific region may be, but is not limited to, the optic nerve papilla region including retinal blood vessels. Finally, The pre-fundus image 73 may be input to the machine learning model 75, and a vascular disease may be predicted by extracting the feature information from the pre-fundus image 73 based on the machine learning model 75.

As depicted in FIG. 7B, in embodiments, First, an enlarged fundus image 70 may be obtained by performing pre-processing on an image like the original fundus image 71 described in FIG. 7A. The pre-processing on the image may be executed by the processor 111 in FIG. 1. After that, the enlarged fundus image 70 may be partially partitioned by a plurality of areas. In this case, each of the plurality of areas may have the same size or different sizes. Each of the plurality of areas may overlap each other locally. At that, a plurality of pre-fundus images 71a, 71b, 71c may be generated according to the partitioned areas. Finally, each of the plurality of pre-fundus images 71a, 71b, 71c may be input to the machine learning model 79 and the vascular disease may be predicted by extracting the feature information from each of the pre-fundus images 71a, 71b, 71c based on the machine learning model 79.

The pre-fundus image may be generated in various ways. For example, the pre-fundus image may be generated by rotating around a reference axis of the original fundus image, or/and the pre-fundus image may be generated by adjusting the contrast or brightness of the original fundus image or/and by flipping around a horizontal or vertical axis of the original fundus image.

Thus, if the pre-fundus image inputs the machine learning model, thereby more improving an accuracy of prediction of the vascular disease.

Figure 8:
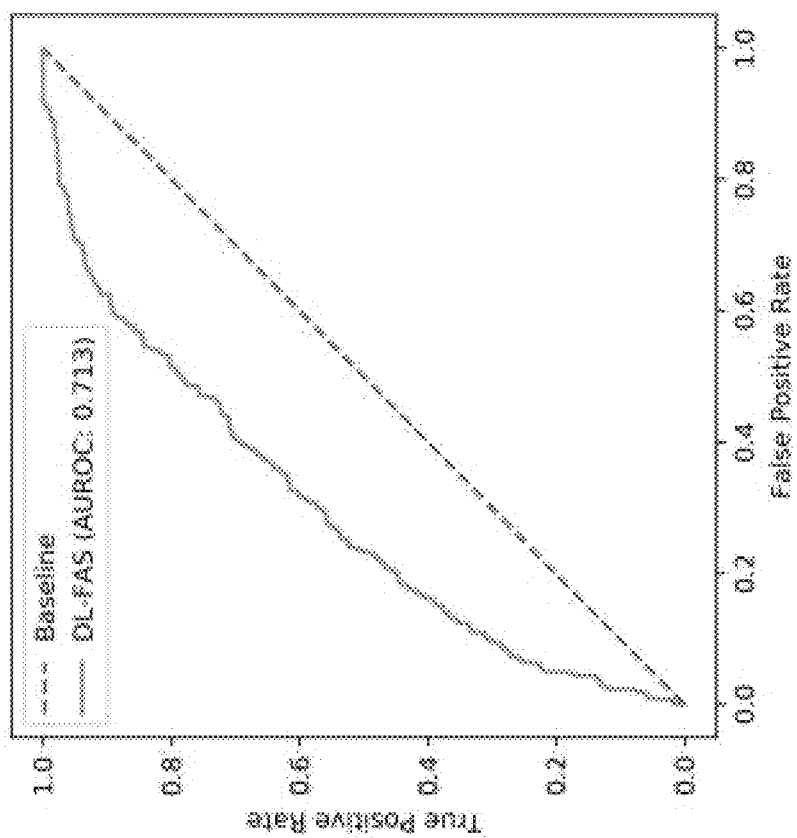
FIG. 8 is a graph showing a prediction accuracy performance of an atherosclerosis obtained based on a machine learning model for a fundus image using an apparatus according to embodiments of the present disclosure.

FIG. 8 is a graph showing a prediction accuracy performance (DL-FAS, AUROC) of atherosclerosis obtained based on a machine learning model for a fundus image using an apparatus according to embodiments of the present disclosure.

As depicted, the machine learning model of the apparatus was trained with the fundus image training set as 12,362 and the fundus image testing set as 1,526. As a result, the prediction accuracy performance value (AUROC) was found to be 0.713. The fundus image used as a training set is an image used in a machine learning model without image pre-processing.

Although the prediction accuracy performance value is not close to the ideal value, the prediction accuracy for vascular disease is sufficiently high. In addition, it is possible to obtain higher prediction accuracy through image pre-processing for the fundus image.

Figure 9:
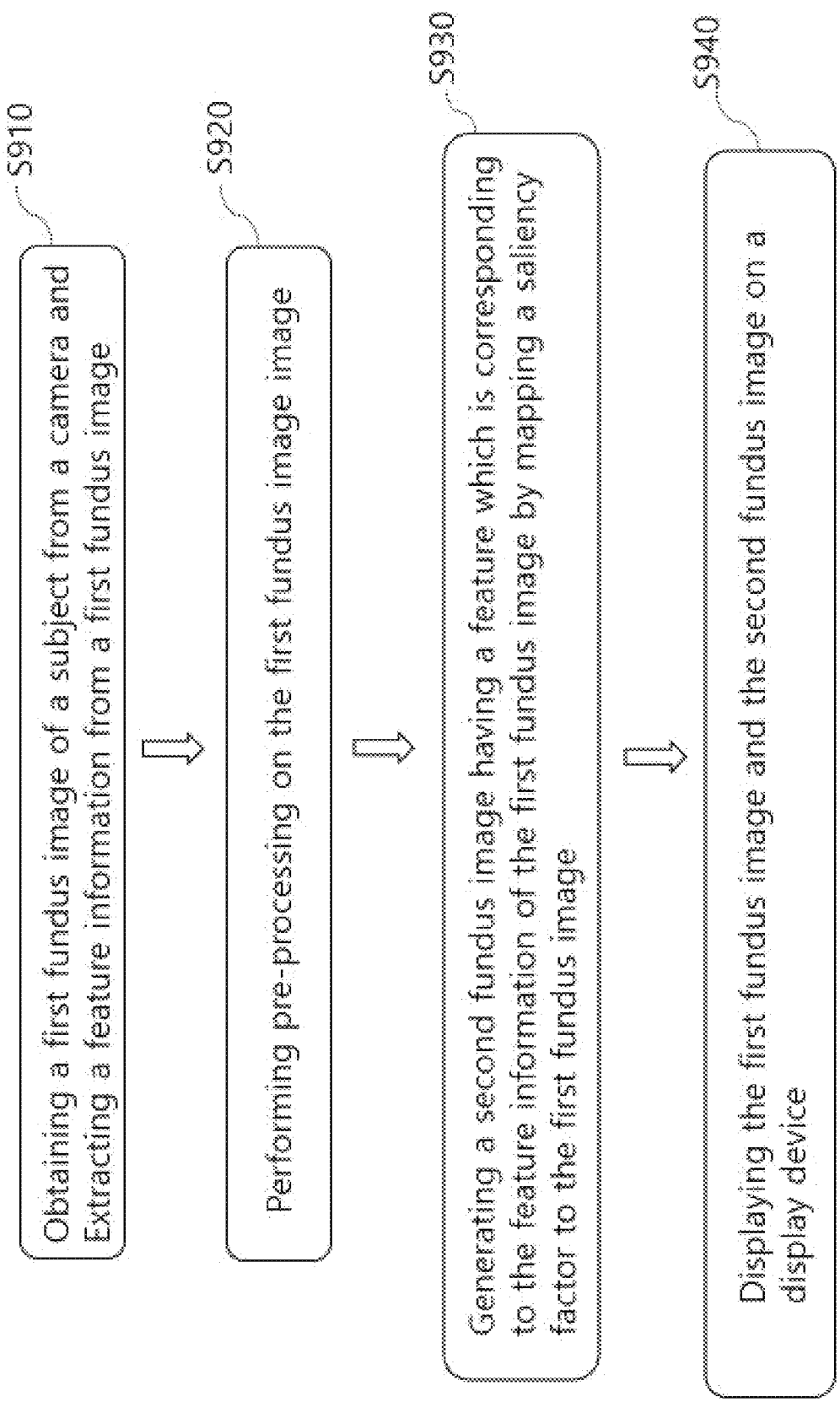
FIG. 9 shows a flowchart illustrating an exemplary process for supporting predicting of vascular disease using a fundus image by a processor according to embodiments of the present disclosure.

FIG. 9 shows a flowchart illustrating an exemplary process for supporting predicting of vascular disease using a fundus image by a processor 111 according to embodiments of the present disclosure.

At step S910, the processor 111 may obtain a first fundus image of a subject from a fundus camera and extract a feature information from the first fundus image of the subject. In embodiments, the first fundus image may be stored in the memory unit 113, 313 or the storage device 115, 315 included to the computing device 110, 310 (as discussed in conjunction with FIGS. 2 and 3). At step S920, the processor 111 may perform image pre-processing on the first fundus image. The method for performing pre-processing on the first fundus image may be similar to pre-processing described in FIG. 7B. At step S930, the processor 111 may map an saliency factor to the first fundus image, thereby generating a second fundus image with a feature which is corresponding to a feature information of the first fundus image. Mapping the saliency factor may be similar to mapping described in FIG. 1. In embodiments, the processor 111 may generate images in which a specific area of the first fundus image and the second fundus image is enlarged. In embodiments, the processor 111 may perform image processing so that the first fundus image and the second fundus overlap, thereby generating a third fundus image is visualized to the user. At step S940, the processor 111 may display the first fundus image and the second fundus image on a display device so as to provide an entity with the feature information and the feature. In embodiments, the processor 111 may display at least one of the enlarged images and the visualized third fundus image on the display device.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. An apparatus for supporting predicting of vascular disease using a fundus image of a subject, comprising:
   a processor; and
   a memory comprising one or more sequences of instructions which, when executed by the processor, causes steps to be performed comprising:
   extracting a feature information from a first fundus image of the subject based on a machine learning model;
   generating a second fundus image having a feature which is corresponding to the feature information by mapping a saliency factor to the first fundus image;
   displaying the first fundus image and the second fundus image on a display device;
   generating images in which a specific area of each of the first fundus image and the second fundus image is enlarged; and
   displaying the images on the display device.

2. The apparatus of claim 1, wherein the steps further comprises:
   generating a third fundus image which is visualized, by performing image processing so that the first fundus image and the second fundus image overlap; and
   displaying the third fundus image on the display device.

3. The apparatus of claim 1, wherein the steps further comprises:
   generating a pre-first fundus image by performing pre-processing on the first fundus image so as to enlarge or partially partition a specific area of the first fundus image.

4. The apparatus of claim 1,
wherein the saliency factor comprises at least one of gradation levels of R, G, and B pixels of the first fundus image, a color of R, G, and B pixels of the first fundus image, and a contrast ratio of the first fundus image.

5. The apparatus of claim 1,
wherein the feature information of the first fundus image includes at least one of information of a retinal vessel change, information of a macular change including a fovea, information of a cotton-wool spot and information of an optic nerve change.

6. The apparatus of claim 5,
wherein the information of the retinal vessel change includes at least one of a thickness of the retinal vessel, an expansion rate of the retinal vessel, a propagation speed of a retinal vessel expansion and a degree of elasticity of the retinal vessel according to the propagation speed of the retinal vessel expansion.

7. The apparatus of claim 5,
wherein the information of the optic nerve change includes at least one of an increased C/D ratio information, a thickness change information for a disc rim thinning and a contrast information for a retinal nerve fiber layer defect.

8. The apparatus of claim 1,
wherein the first feature information is extracted by utilizing a clinical information of the subject.

9. A non-transitory computer-readable medium or media comprising one or more sequences of instructions which, when executed by a processor, causes steps for supporting predicting of vascular disease using a fundus image of a subject, comprising:
   extracting a feature information from a first fundus image of the subject based on a machine learning model;
   generating a second fundus image having a feature which is corresponding to the feature information by mapping a saliency factor to the first fundus image;
   displaying the first fundus image and the second fundus image on a display device;
   generating images in which a specific area of each of the first fundus image and the second fundus image is enlarged; and
   displaying the images on the display device.

10. The non-transitory computer-readable medium or media of claim 9, wherein the steps further comprises:
   generating a third fundus image which is visualized, by performing image processing so that the first fundus image and the second fundus image overlap; and
   displaying the third fundus image on the display device.

11. The non-transitory computer-readable medium or media of claim 9, wherein the steps further comprises:
   generating a pre-first fundus image by pre-processing on the first fundus image so that a specific area of the first fundus image is enlarged or partially partitioned.

12. A method for supporting reading of a fundus image of a subject, comprising:
   extracting a feature information from a first fundus image of the subject based on a machine learning model;
   generating a second fundus image having a feature which is corresponding to the feature information by mapping a saliency factor to the first fundus image;
   displaying the first fundus image and the second fundus image on a display device;
   generating images in which a specific area of each of the first fundus image and the second fundus image is enlarged; and
   displaying the images on the display device.

13. The method of claim 12, further comprising:
   generating a third fundus image which is visualized, by performing image processing so that the first fundus image and the second fundus image overlap; and
   displaying the third fundus image on the display device.

14. The method of claim 12, further comprising:
   generating a pre-first fundus image by pre-processing on the first fundus image so that a specific area of the first fundus image is enlarged or partially partitioned.

* * * * *